US007615081B2

(12) United States Patent
Justin et al.

(10) Patent No.: US 7,615,081 B2
(45) Date of Patent: Nov. 10, 2009

(54) FEMORAL COMPONENTS FOR KNEE ARTHROPLASTY

(75) Inventors: Daniel F. Justin, Logan, UT (US); E. Marlowe Goble, Alta, WY (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 10/444,927

(22) Filed: May 23, 2003

(65) Prior Publication Data

US 2003/0225457 A1  Dec. 4, 2003

Related U.S. Application Data

(60) Provisional application No. 60/383,348, filed on May 24, 2002.

(51) Int. Cl.
*A61F 2/38* (2006.01)
(52) U.S. Cl. .................................. 623/20.14
(58) Field of Classification Search ............. 623/18.11, 623/20.1–20.36; 606/88
See application file for complete search history.

(56) References Cited

U.S. PATENT DOCUMENTS

| | | | |
|---|---|---|---|
| 4,081,866 A | 4/1978 | Upshaw et al. | |
| 4,217,666 A | 8/1980 | Averill | |
| 4,224,696 A | 9/1980 | Murray | |
| 4,309,778 A | 1/1982 | Buechel et al. | |
| 4,340,978 A | 7/1982 | Buechel et al. | |
| 4,470,158 A | 9/1984 | Pappas et al. | |
| 4,479,271 A | 10/1984 | Bolesky et al. | |
| 4,502,161 A | 3/1985 | Wall | |
| 4,627,853 A | 12/1986 | Campbell et al. | |
| 4,662,889 A | 5/1987 | Zichner et al. | |
| 4,673,407 A | 6/1987 | Martin | |
| 4,822,366 A | 4/1989 | Bolesky | |
| 5,037,439 A | 8/1991 | Albrektsson et al. | |
| 5,092,895 A | 3/1992 | Albrektsson et al. | |
| 5,100,409 A | 3/1992 | Coates et al. | |

(Continued)

FOREIGN PATENT DOCUMENTS

DE    3 917 285 A1    11/1990

(Continued)

OTHER PUBLICATIONS

AGC Total Knee System, *Patellar Femoral Systems*, by Biomet Inc.
Whiteside Ortholoc Modular Knee System, *Total Condylar*, Dow Corning Wright Publication, 1990.
Implants, 1990.
Miller/Galante, *Unicompartmental Knee System Implants and Instruments*, By Zimmer.
P.F.C. Total Knee System, Johnson & Johnson Orthopaedics, Sep. 1988.
The Miller/Galante Advantage, *Unicompartmental Knee System*, by Zimmer.

(Continued)

*Primary Examiner*—Eduardo C Robert
*Assistant Examiner*—David Comstock
(74) *Attorney, Agent, or Firm*—Baker & Daniels LLP

(57) ABSTRACT

A femoral knee prosthesis system for resurfacing a resected articular surface at the distal end of a femur includes a femoral component adapted to mate with the resected articular surface; and an attachment member. The interior surface of the femoral component is configured to connect to the first attachment member when the femoral component is mated on the resected articular surface of the femur and when the first attachment member is passed through the medial side or the lateral side of the resected articular surface. The femoral component is available in one-piece and two-piece systems. Mating femoral components (e.g., tapered or with lips that interlock with grooves) are also disclosed.

18 Claims, 10 Drawing Sheets

U.S. PATENT DOCUMENTS

| | | |
|---|---|---|
| 5,116,375 A | 5/1992 | Hofmann |
| 5,122,144 A | 6/1992 | Bert et al. |
| 5,123,928 A | 6/1992 | Moser |
| 5,147,406 A | 9/1992 | Houston et al. |
| 5,176,684 A | 1/1993 | Ferrante et al. |
| 5,181,925 A | 1/1993 | Houston et al. |
| 5,226,916 A | 7/1993 | Goodfellow et al. |
| 5,258,032 A | 11/1993 | Bertin |
| 5,282,868 A | 2/1994 | Bahler et al. |
| 5,312,411 A | 5/1994 | Steele et al. |
| 5,330,534 A | 7/1994 | Herrington et al. |
| 5,358,529 A | 10/1994 | Davidson |
| 5,358,530 A | 10/1994 | Hodorek |
| 5,405,395 A | 4/1995 | Coates |
| 5,405,398 A | 4/1995 | Buford, III et al. |
| 5,549,684 A | 8/1996 | Amino et al. |
| 5,549,688 A | 8/1996 | Ries et al. |
| 5,556,433 A | 9/1996 | Gabriel et al. |
| 5,569,259 A | 10/1996 | Ferrante et al. |
| 5,702,464 A | 12/1997 | Lackey et al. |
| 5,702,466 A | 12/1997 | Pappas et al. |
| 5,725,584 A | 3/1998 | Walker et al. |
| 5,728,162 A | 3/1998 | Eckhoff |
| 5,755,800 A | 5/1998 | O'Neil et al. |
| 5,755,803 A | 5/1998 | Haines et al. |
| 5,766,255 A | 6/1998 | Slamin et al. |
| 5,769,855 A | 6/1998 | Bertin et al. |
| 5,776,201 A | 7/1998 | Colleran et al. |
| 5,782,925 A | 7/1998 | Callazo et al. |
| 5,824,105 A | 10/1998 | Ries et al. |
| 5,871,545 A | 2/1999 | Goodfellow et al. |
| 5,879,391 A | 3/1999 | Slamin |
| 5,902,340 A | 5/1999 | White et al. |
| 5,906,643 A | 5/1999 | Walker |
| 5,911,758 A | 6/1999 | Oehy et al. |
| 5,964,808 A | 10/1999 | Blaha et al. |
| 6,013,103 A | 1/2000 | Kaufman et al. |
| 6,077,270 A | 6/2000 | Katz |
| 6,123,729 A | 9/2000 | Insall et al. |
| 6,126,693 A | 10/2000 | O'Neil et al. |
| 6,132,468 A | 10/2000 | Mansmann |
| 6,165,223 A | 12/2000 | Metzger et al. |
| 6,168,629 B1 | 1/2001 | Timoteo |
| 6,171,340 B1 | 1/2001 | McDowell |
| 6,171,342 B1 | 1/2001 | O'Neil et al. |
| 6,190,415 B1 | 2/2001 | Cooke et al. |
| 6,197,064 B1 | 3/2001 | Haines et al. |
| 6,214,051 B1 | 4/2001 | Badorf et al. |
| 6,214,952 B1 | 4/2001 | Sadatoshi et al. |
| 6,235,060 B1 | 5/2001 | Kubein-Meesenburg et al. |
| 6,245,110 B1 | 6/2001 | Grundei et al. |
| 6,299,645 B1 | 10/2001 | Ogedn |
| 6,364,911 B1 | 4/2002 | Schmotzer et al. |
| 6,383,222 B1 | 5/2002 | Badorf |
| 6,402,786 B1 | 6/2002 | Insall et al. |
| 6,482,209 B1 | 11/2002 | Engh et al. |
| 6,589,283 B1 | 7/2003 | Metzger et al. |
| 6,743,258 B1 | 6/2004 | Keller |
| 6,749,638 B1 | 6/2004 | Saladino |
| 2001/0016778 A1 | 8/2001 | Badorf et al. |
| 2002/0022890 A1 | 2/2002 | Jacobsson et al. |
| 2002/0138150 A1 | 9/2002 | Leclercq |
| 2002/0198528 A1 | 12/2002 | Engh et al. |
| 2003/0004577 A1 | 1/2003 | Running |
| 2003/0028196 A1 | 2/2003 | Bonutti |
| 2003/0093156 A1 | 5/2003 | Metzger et al. |
| 2003/0153977 A1 | 8/2003 | Suguro et al. |
| 2003/0153979 A1 | 8/2003 | Hughes et al. |
| 2003/0158606 A1 | 8/2003 | Coon et al. |
| 2003/0225458 A1 | 12/2003 | Donkers et al. |
| 2004/0102582 A1 | 5/2004 | Dang et al. |
| 2004/0117023 A1 | 6/2004 | Gerbec et al. |
| 2004/0117024 A1 | 6/2004 | Gerbec et al. |
| 2004/0143336 A1 | 7/2004 | Burkinshaw |

FOREIGN PATENT DOCUMENTS

| | | |
|---|---|---|
| DE | 197 16 879 A1 | 11/1998 |
| DE | 19716879 A1 | 11/1998 |
| DE | 69528655 T2 | 7/2003 |
| EP | 0 336 774 A1 | 10/1989 |
| EP | 0 376 658 A3 | 7/1990 |
| EP | 0 502 737 B1 | 9/1992 |
| EP | 0 600 806 B1 | 6/1994 |
| EP | 0 674 887 | 10/1995 |
| EP | 0 674 887 B1 | 10/1995 |
| EP | 0 522 822 B1 | 12/1995 |
| EP | 0 714 645 B1 | 6/1996 |
| EP | 0 731 676 B1 | 9/1996 |
| EP | 0 749 734 B1 | 12/1996 |
| EP | 0 781 117 B1 | 7/1997 |
| EP | 0 850 606 A | 7/1998 |
| EP | 0 891 756 A2 | 1/1999 |
| EP | 0 916 322 A2 | 5/1999 |
| EP | 0 913 135 A3 | 6/1999 |
| EP | 0 941 719 A2 | 9/1999 |
| EP | 0 985 386 A2 | 3/2000 |
| EP | 0 986 994 A2 | 3/2000 |
| EP | 1 216 669 A3 | 6/2002 |
| EP | 1 245 204 A3 | 10/2002 |
| EP | 1 348 408 A2 | 10/2003 |
| EP | 1 380 273 A2 | 1/2004 |
| FR | 2 521 421 A | 8/1983 |
| FR | 2 682 287 | 4/1993 |
| FR | 2 682 589 A | 4/1993 |
| FR | 2 718 953 | 10/1995 |
| GB | 2 007 980 A1 | 5/1979 |
| GB | 2 355 935 A | 5/2001 |
| WO | WO 87/02882 | 5/1987 |
| WO | WO 87/02882 A1 | 5/1987 |
| WO | WO 89/11837 | 12/1989 |
| WO | WO 91/06260 | 5/1991 |
| WO | WO 94/09723 | 5/1994 |
| WO | WO 95/14446 | 6/1995 |
| WO | WO 98/02116 A1 | 1/1998 |
| WO | WO 98/20818 A1 | 5/1998 |
| WO | WO 99/13803 | 3/1999 |
| WO | WO 99/13803 A2 | 3/1999 |
| WO | WO 99/32053 | 7/1999 |
| WO | WO 00/23010 | 4/2000 |
| WO | WO 00/23011 A1 | 4/2000 |
| WO | WO 01/06961 A1 | 2/2001 |
| WO | WO 01/34069 A1 | 5/2001 |
| WO | WO 01/70142 A1 | 9/2001 |
| WO | WO 03/070127 A1 | 8/2003 |
| WO | WO 2004/037119 A2 | 5/2004 |

OTHER PUBLICATIONS

*Patellar Resurfacing with Specialist Instruments in Total Knee Arthroplasty, Surgical Technique*, Johnson & Johnson Orthopaedics.

Aaron A. Hofmann, M.D. et al., *Surgical Technique the Intermedics Natural-Knee System*, Intermedics Orthopedics, Salt Lake City, Utah 1986.

The Intermedics Natural-Knee System with Cancellous-Structured Titanium, 1987.

Gerard A. Engh et al., *The AMK Total Knee System, Design Rationale and Surgical Procedure*, DePuy 1988.

Whiteside Ortholoc Modular Knee System, *Surgical Procedure for the Whiteside Ortholoc Modular Knee System*, Dow Corning Wright, 1990.

*Surgical Technique, Genesis Total Knee System Posterior—Stabilized*, Smith+Nephew Richards.

FEMORAL COMPONENTS FOR KNEE ARTHROPLASTY

CROSS-REFERENCE TO RELATED APPLICATIONS

This nonprovisional patent application claims priority to a provisional patent application entitled MODULAR FEMORAL COMPONENTS FOR TOTAL KNEE ARTHROPLASTY, to E. Marlowe Goble and Daniel F. Justin, filed on May 24, 2002, Ser. No. 60/383,348 which is incorporated herein in its entirety by reference.

BACKGROUND OF THE INVENTION

1. The Field of the Invention

The present invention relates to femoral components for use in total knee arthroplasty.

2. Background Technology

During a typical knee arthroplasty procedure, the femur is resected with surgical instruments in order to form a resected femoral portion, also known as a resected femur. A femoral component typically in the form of a metal cap is then placed onto the resected femur. The femoral component is typically designed to interact with and articulate against a tibial component that is mounted onto the resected tibia.

During the arthroplasty procedure, the femoral component is inserted through an incision onto the resected femur. The larger and bulkier the femoral component is, the larger the incision is required to be, thus increasing the recovery time of the patient, thus increasing the pain associated with the surgery and the recovery time.

Depicted in FIGS. 1 and 2 is one embodiment of a prosthetic femoral component 10 having an interior surface 12 and an exterior surface 14. Interior surface 12 is comprised of a plurality of intersecting substantially flat surfaces that correspond to discrete cut surfaces on a femur. Pegs 16a-b project from interior surface 12 for engaging with the femur. Pegs 16a-b are designed to be implanted within the resected femur, thereby anchoring the femoral component to the femur. The exterior surface 14 articulates against the tibial component.

However, the pegs are affixed using a compression fit into the resected femur and project from the interior surface, thereby adding to the bulkiness and size of the femoral component, thereby requiring a larger incision during surgery.

What is therefore needed is a femoral component for use in a knee arthroplasty procedure that is not bulky and does not require a large incision during surgery. What is also needed is a femoral component that is firmly affixed to the resected femur and is convenient to mount thereon.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
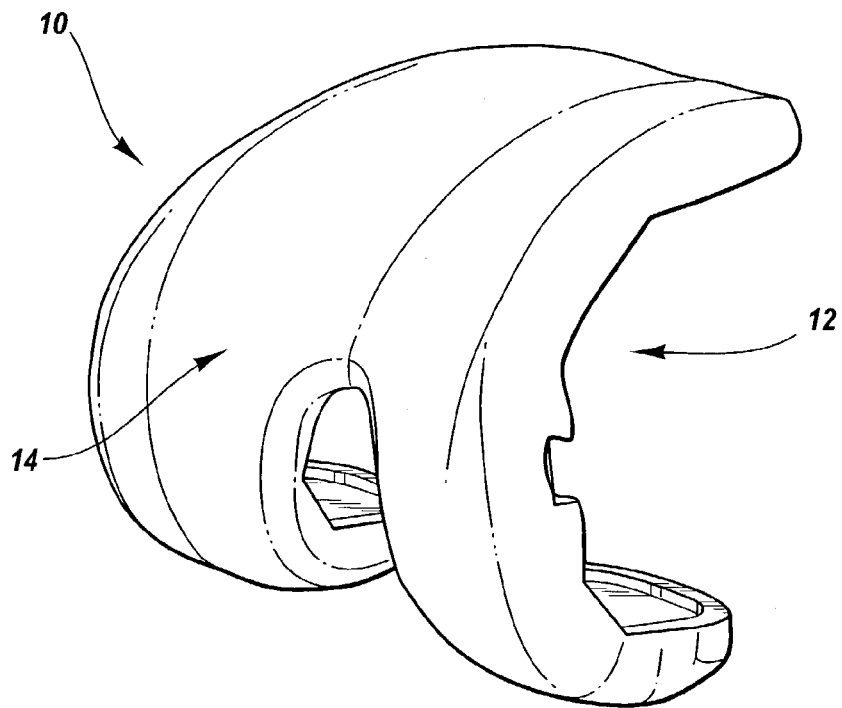
FIG. 1 is a front perspective view of a prior art femoral component.
Figure 2:
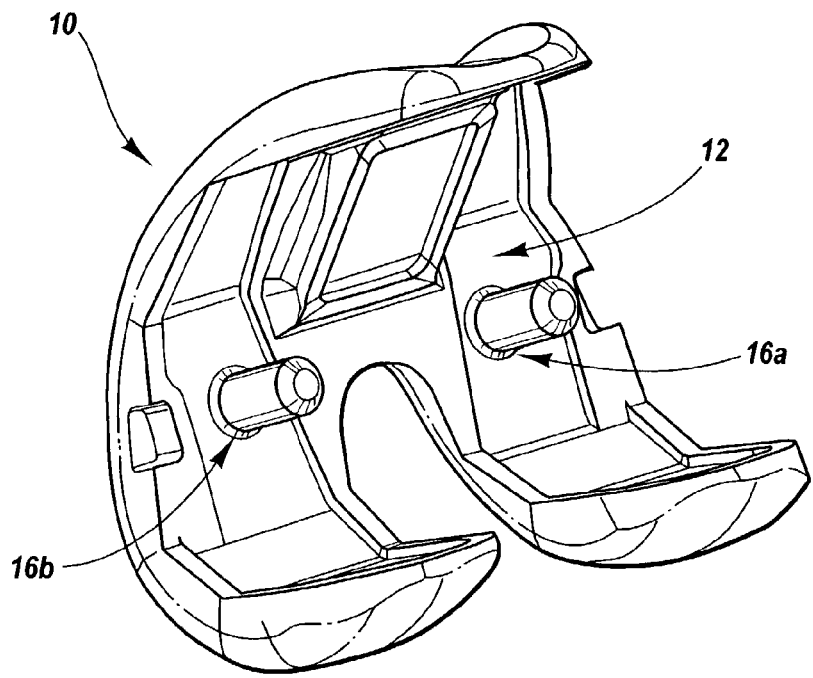
FIG. 2 is a back perspective view of the prior art femoral component shown in FIG. 1.
Figure 3:
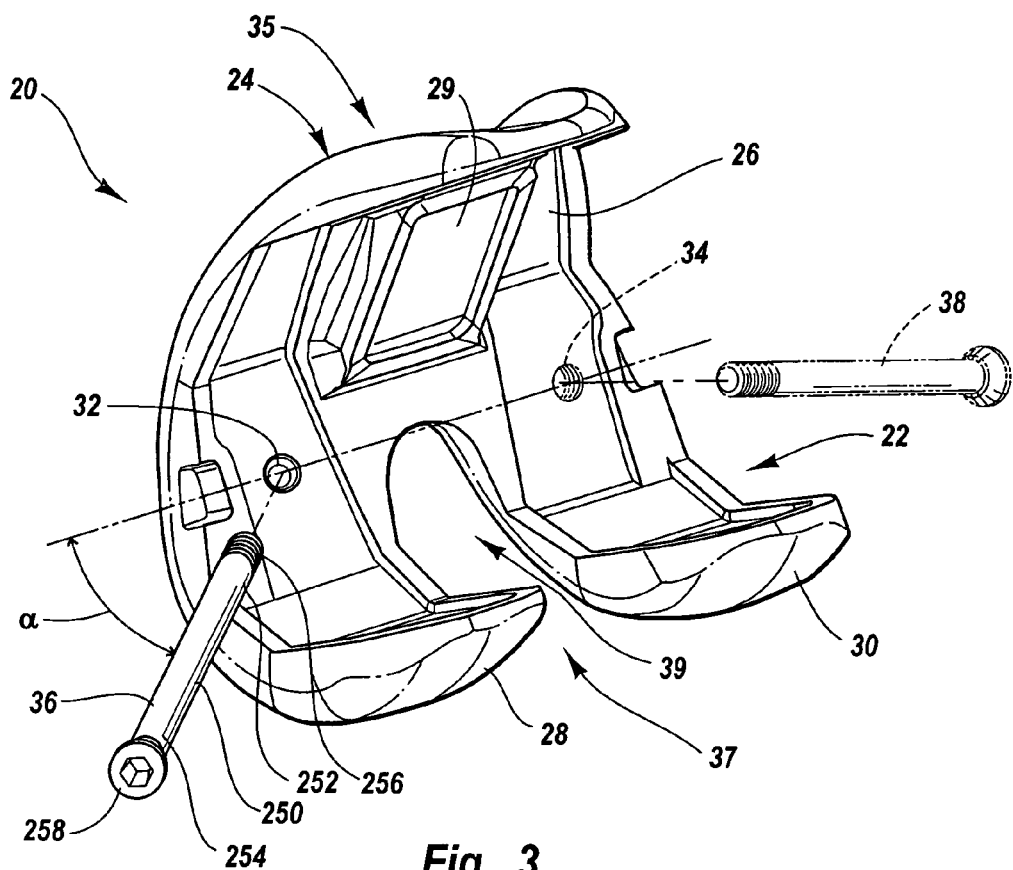
FIG. 3 is a back perspective view of a femoral component of the present invention featuring at least one threaded bore formed on the interior surface thereof that is configured to receive an attachment member extended through the resected femur; an optional second threaded bore and attachment member are shown in phantom lines; the attachment member may be extended through the medial and/or lateral side.
Figure 4:
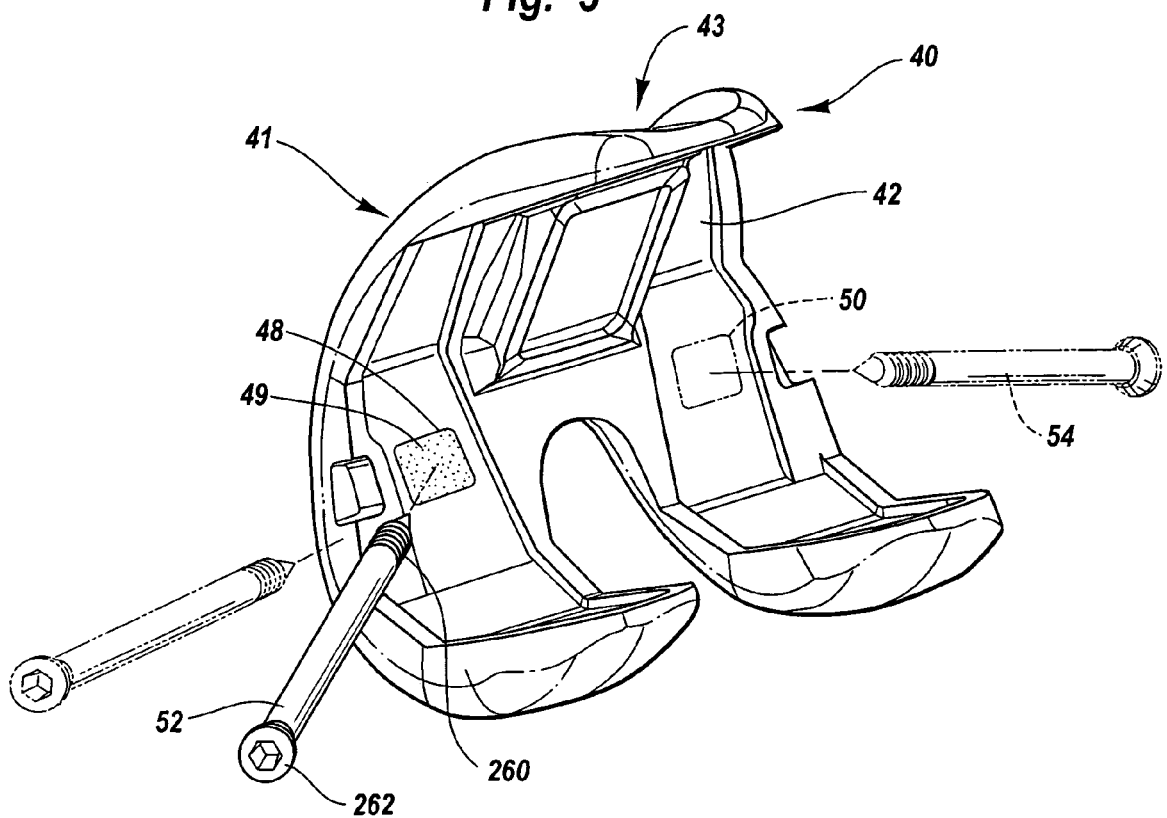
FIG. 4 is a back perspective view of another femoral component of the present invention featuring at least one engaging, receiving pocket filled with a receiving, engaging material that receives and engages at least one attachment member extended through the resected femur; an optional additional receiving surface and attachment member(s) are shown in phantom lines.
Figure 5:
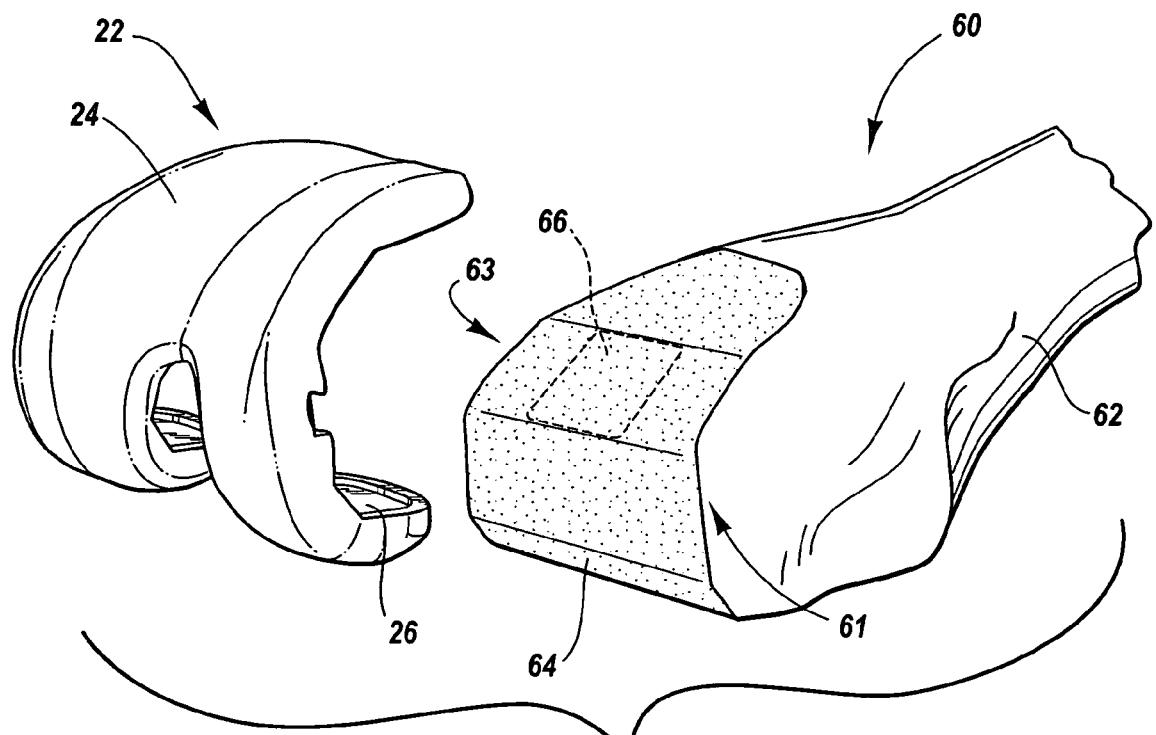
FIG. 5 is a perspective view of the femoral component of FIG. 3 being mounted on a resected femur; a receiving surface 66 for an optional plate 29 of the femoral component is shown in phantom lines.

FIGS. 3-6 depict examples of femoral knee prosthesis systems used in knee arthroplasty wherein the femoral components are readily slid in from the medial or lateral side through an incision and onto a femoral resection 60 (FIG. 5). An attachment member, such as a bolt or screw can then be inserted through the femur until contacting the femoral component. The procedure is minimally invasive and does not require as large an incision as components having the pegs 16a-b of FIG. 2. The bolt, screw or other attachment member securely affixes the femoral component to the resected femur, rather than merely relying upon a compression fit.

Figure 7:
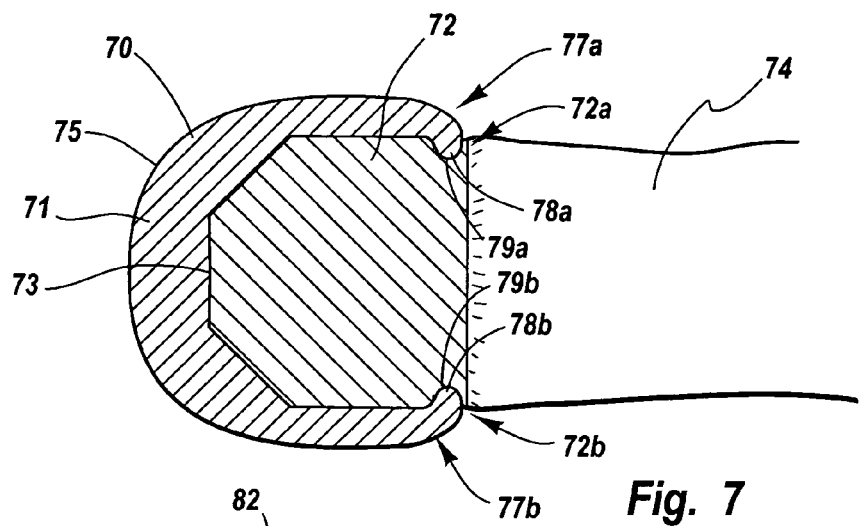
FIG. 7 is a side cross sectional view of an alternative embodiment of a femoral component having inwardly projecting lips shown as being mounted within corresponding grooves cut into a resected femur, thereby securing the femoral component to the resected femur.
Figure 8:
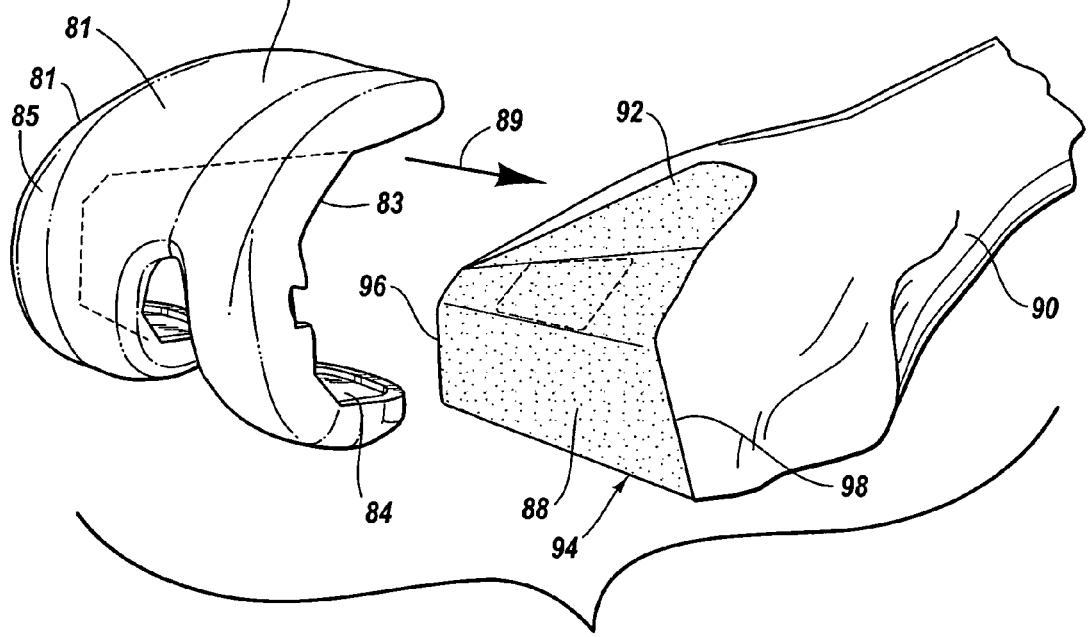
FIG. 8 is a perspective view of a femoral component having a tapered interior surface that is being mounted onto a resected femur having a complimentary, tapered, mating surface, thereby securing the femoral component to the resected femur.
Figure 8A:
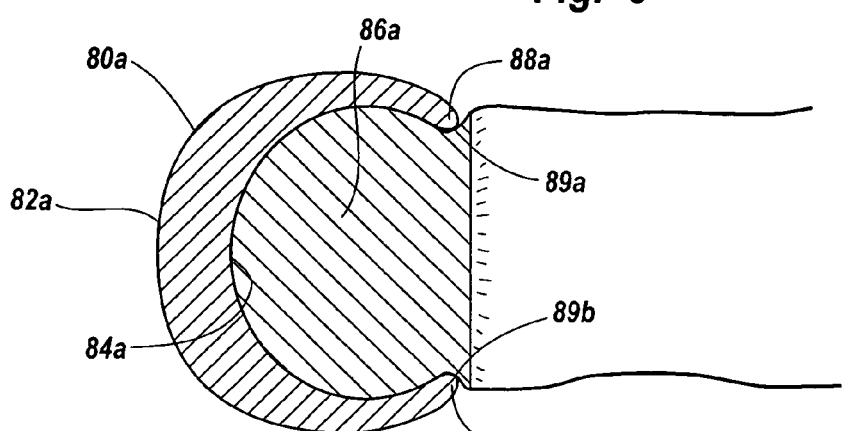
FIG. 8a is a cross sectional view of an alternative femoral component, having a non-chamfered, curved surface, shown as mounted onto a resected femur, demonstrating that a femoral component having inwardly projecting lips can have a variety of different interior surfaces.

FIGS. 7-8A depict examples of femoral components 70, 80 used in knee arthroplasty wherein a mating relationship, e.g., mating lips 78a-b and grooves 79a-b (FIG. 7) or mating tapering surfaces (FIG. 8) maintain the femoral component on the resected femur.

FIGS. 9-14 depict connectible two-piece end use femoral components 102, 131, 161, and 191 used in knee arthroplasty wherein the two parts are readily, independently slid in from the medial or lateral side through an incision and then connected and mounted onto a femoral resection. Optionally, one part may be mounted on the femoral resection followed by another part being connected thereto. Both parts may also be first mounted, then connected together. An attachment member, such as a bolt or screw can then be inserted through the femur until contacting the femoral component. Optionally, bone cement can be employed to cement the femoral component to the resected femur.

A coupling member, e.g., a bolt or a screw attaches one part of the femoral component to another. The procedure is minimally invasive and does not require as large an incision as one piece components because one part of the femoral component may be placed through the incision, followed the other part of the femoral component. The individual pieces of the femoral component themselves may also be employed without the corresponding mating piece, such as when only a portion (e.g., a tibial portion) of the component is needed for a particular procedure.

FIGS. 15A-16B depict a connectible two-piece end use femoral component 210 used in knee arthroplasty wherein the two parts are readily, independently slid in from the medial or lateral side through an incision and then connected and mounted onto a femoral resection. Optionally, one part may be mounted on the femoral resection followed by another part being connected thereto. Integral protrusions extending from one part attach the one part of the femoral component to the other. The procedure is minimally invasive and does not require as large an incision as one piece components because one part of the femoral component may be placed through the incision, followed the other part of the femoral component. Pegs are employed for anchoring the component on a femoral resection.

Each of these femoral components will now be discussed in greater detail beginning with reference to FIGS. 3, 5, and 6. FIG. 3 is a back perspective view of a femoral knee prosthesis system 20 for resurfacing a resected articular surface 64 (FIG. 5) at the distal end 62 of a femur 60. As shown in FIG. 5, the resected articular surface 64 of the distal end 62 of the femur 60 has a medial side 61 and an opposing lateral side 63.

Prosthesis system 20 of FIG. 3 comprises: (i) a U-shaped femoral component 22 having (i) an interior surface 26 adapted to mate with the resected articular surface 64 and (ii) an opposing articulating surface 24; (ii) a first attachment member, e.g., elongated bolt 36 having a threaded end; and (iii) a threaded bore 32 formed on interior surface 26 of femoral component 22. Bolt 36 is shown having an elongated shaft 250 extending between a first end 252 and an opposing second end 254. Threads 256 are formed at first end 252 while an enlarged head 258 is positioned at second end 254.

Threaded bore 32 is blind and is an example of means formed on the interior surface 26 of the femoral component 22 for connecting the first attachment member 36 to the femoral component 22 when the femoral component 22 is mated on the resected articular surface 64 of the femur 60 and when the first attachment member 36 is passed through the medial side or the lateral side of the resected articular surface 64.

Figure 6:
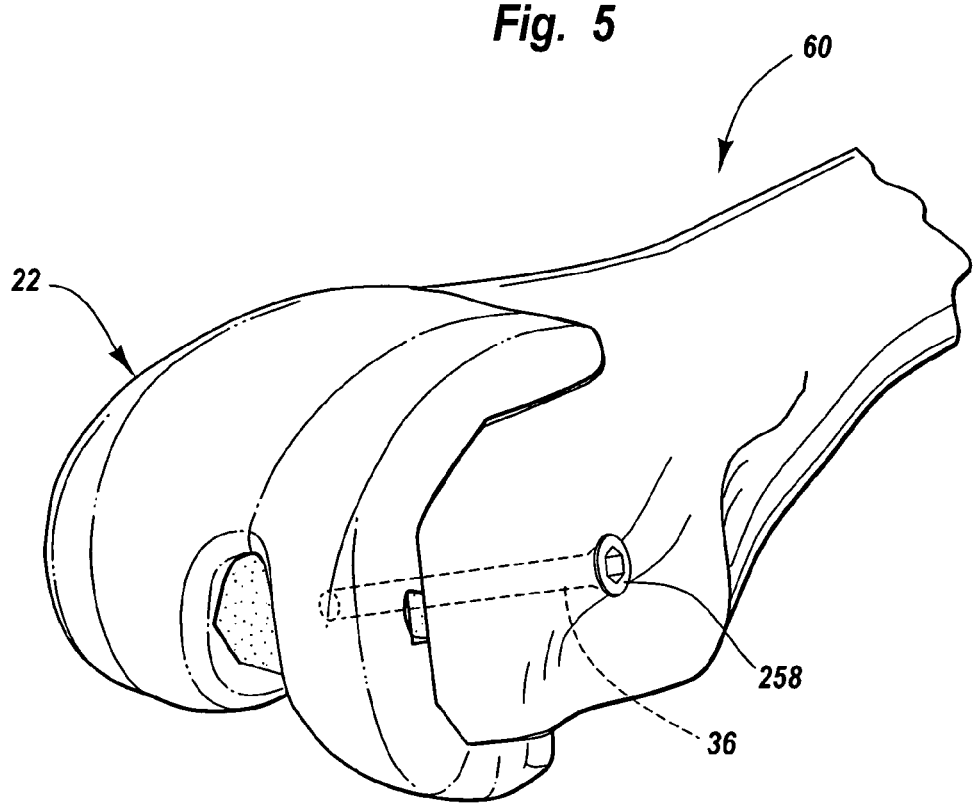
FIG. 6 is a perspective view of the femoral component of FIGS. 3 and 5 shown as being mounted on the resected femur of FIG. 5 and having an attachment member (shown primarily in phantom lines) extended through the resected femur and into the femoral component, thereby securing the femoral component to the femur.

Threaded bore 32 is angled such that when femoral component 22 is mated on the resected articular surface of femur 60, bolt 36 can be passed through medial side 61 or lateral side 63 of the resected articular surface 64 so as to threadedly engage with the threaded bore 32 (see FIGS. 5-6).

Femoral component 22 comprises a substantially U-shaped medial condyle 28 connected to a substantially U-shaped lateral condyle 30. Femoral component has an anterior end 35 and a posterior end 37. The medial condyle 28 is connected to the lateral condyle 30 such that an elongated slot 39 is formed between the lateral condyle and the medial condyle. However, in another embodiment, the femoral component of the present invention comprises merely a substantially U-shaped lateral condyle or a substantially U-shaped medial condyle, depending upon the desired procedure.

An optional plate 29 of the femoral component 22 may be employed to provide differential surface area for engagement with a complementary surface on the prosthesis.

As further shown in FIG. 3, system 20 comprises (i) an optional second attachment member 38; and (ii) means (e.g., second threaded bore 34) formed on the interior surface 26 of the femoral component 22 for connecting the second attachment member 38 to the femoral component 22 when the femoral component 22 is mated on the resected articular surface 64 of the femur 60 and when the second attachment member 38 is passed through the medial side or the lateral side of the resected articular surface 64.

Optionally, another attachment member may extend into the medial, anterior surface into another threaded bore adjacent bore 32, if desired.

Screws, bolts, pins or other forms of fasteners that can be driven through femur 60 so as to engage with interior surface 26 of femoral component 22 are each examples of attachment members of the present invention. One or more attachment members 36, 38 may attach to respective one or more bores 32, 34. In one embodiment, the attachment members are on opposing sides of the femoral component from each other, as shown in FIG. 3. As mentioned, in another embodiment, the attachment members mount into the same side of the femoral component (see also FIG. 4). These attachment members can engage with interior surface 26 by having threaded bores (FIG. 3) or by positioning receiving, engaging material on interior surface 42 to which the fasteners can penetrate and engage with, as will now be discussed with reference to FIG. 4.

FIG. 4 is a back perspective view of another femoral knee prosthesis system 40 comprising (i) a femoral component 41 comprising an interior surface 42 adapted to mate with the resected articular surface 64 and an opposing articulating surface 43; (ii) a first attachment member, e.g., elongated screw 52 having a threaded end 260 and an enlarged head 262; and (iii) a pocket 48 formed on interior surface 42 of femoral component 41.

Femoral component 41 has at least one pocket 48 (filled with an engaging, receiving material 49) that receives at least one attachment member 52 extended through the resected femur 60; an optional additional pocket 50 and an additional corresponding attachment member 54 are shown in phantom lines. Pockets 48, 50 filled with such material are additional examples of means formed on the interior surface 42 of the femoral component 41 for connecting an attachment member to the femoral component.

Pockets 48, 50 are formed on the interior surface 42 of the femoral component 41 and are filled with an engaging, receiving material, such as an adhesive (e.g., polymethylmethacrylate) or another material that is soft enough to receive the attachment member, but can also retain the attachment member therein. Other examples of such a receiving, engaging material include pliable polymers such as Delrin or polyetheretherketone that are capable of receiving and deforming to the shape of the first attachment member.

In one embodiment, in addition to the use of a bolt or screw to attach the femoral component to the prosthesis, a bone cement can be employed to further enhance the adhesion of the femoral component to the resected femur. The bone cement can be applied before and/or during mounting of the femoral component. For example, the femoral component can be partially attached and then a syringe or other form of delivery tube used to inject bone cement between the femoral component and the femur. In addition, a porous or fibrous material such as a wire mesh may be attached to the interior surface 26 of the femoral component 22 to thereby foster bone growth between the femoral component 22 and the resected femur 60 and to provide surface area for attaching the bone cement between the femoral component and the resected femur.

FIG. 5 is a persective view of the femoral component 22 of FIG. 3 being mounted on a resected femur 60. A complimentary receiving surface 66 for the optional plate 29 of the femoral component is shown in phantom lines.

FIG. 6 is a perspective view of the femoral component 22 of FIGS. 3 and 5 shown as being mounted on the resected femur 60 of FIG. 5 and having an attachment member 36 (shown primarily in phantom lines) extended through the resected femur 60 and into the femoral component 22, thereby securing the femoral component 22 to the femur 60. This attachment tightly pulls the femoral component 22 toward and onto the femur 60.

FIGS. 5 and 6 also illustrate a method for resurfacing a femur as part of a surgical procedure, comprising (i) resecting an articulating surface 64 at a distal end 62 of a femur 60 so as to form a resected articular surface 64 extending between a medial side 61 and a lateral side 63; (ii) mounting a femoral component 22 having an interior surface 26 on at least a portion of the resected articular surface 64; (iii) passing a first attachment member 36 through the lateral side or the medial side of the resected articular surface 64; and (iv) connecting the first attachment member 36 to the femoral component 22 so that the first attachment member 36 secures the femoral component 22 to the resected articular surface 64.

In one embodiment, the act of resecting an articulating surface comprises resecting a medial condyle and a lateral condyle at the distal end of the femur. In FIG. 5, the medial and lateral condyles of femur 60 have been resected. As discussed above, femoral component 22 comprises a substantially U-shaped lateral condyle connected to a substantially U-shaped medial condyle.

In another embodiment, the act of resecting an articulating surface 64 comprises resecting only a medial condyle or only a lateral condyle at the distal end 62 of the femur 60, without the other of the medial condyle or lateral condyle being resected. In such an alternate embodiment, the act of mounting a femoral component on at least a portion of the resected articular surface 64 comprises the femoral component being a unicondular lateral condyle or medial condyle.

In one embodiment, the act of passing a first attachment member 36 through the lateral side or the medial side of the resected articular surface 64 comprises: (i) boring a hole through the femur; and (ii) advancing the first attachment member 36 through the hole. The hole can be bored through the femur at an oblique angle α, as reflected in FIGS. 3 and 6. The hole can be bored by making an incision in the skin adjacent to the femur, properly oriented a tubular alignment guide, then boring the hole with a drill through the alignment guide. Optionally, however, the first attachment member is advanced through the femur at such an angle α (e.g., by being advanced through a tubular alignment guide used to orient the first attachment member) without initially boring a hole therethrough. In one embodiment the angle α is in the range of approximately 15 to approximately 45 degrees, e.g., about 30 degrees, but may be a variety of different angles which achieve the result of affixing the femoral component to the femur.

The method of resurfacing the femur may further comprise (i) passing a second attachment member 38 (FIG. 3) through the lateral side or the medial side of the resected articular surface; and (ii) connecting the second attachment member 38 to the femoral component 22 so that the second attachment member 38 secures the femoral component 22 to the resected articular surface.

As discussed above, FIGS. 7-8A depict examples of femoral components 70, 80 wherein a mating relationship between the femoral component and the resected femur maintains the femoral component on the resected femur. The prosthetic femoral component can come in a variety of alternative configurations.

FIG. 7 is a side cross sectional view of femoral component 70, which comprises a "U" shaped main body 71 having an interior surface 73 an exterior surface 75, an anterior end 77*a*, and a posterior end 77*b*, and anterior and posterior inwardly projecting lips 78*a*, 78*b*, respectively, extending from an interior surface 73 of the main body 71. As shown, lips 78*a-b* are mounted within corresponding grooves 79*a*, 79*b* cut into a resected femur 74, thereby securing the femoral component 70 to the resected portion 72 of the femur 74. In one embodiment, main body 71 has the same or substantially the same configuration as the femoral component 22 shown in FIGS. 3, 5 and 6, but has lips 78*a-b* projecting inwardly from the interior surface 73 of respective posterior and anterior ends 77*a-b* thereof. Groove 79*a* is formed in an anterior surface 72*a* of the femur, while groove 79*b* is formed in a posterior surface 72*b* of the femur.

The lips 78*a-b* may project inwardly from one or more condyles. For example, one posterior lip 78*b* may extend from a medial condyle while another posterior lip 78*b* extends from a lateral condyle. Optionally, posterior lips 78*b* may extend from the lateral and the medial condyle. FIG. 7 is representative of a posterior lip 78*b* extending from the interior surface of the lateral and/or medial condyle.

Similarly, the anterior lip 78*a* may extend from the interior surface 73 of the anterior end 77*a* of the lateral or medial condyle, or may extend as a single lip from the interior surface of both the anterior end of the medial condyle and the anterior end of the lateral condyle.

Thus, in one embodiment, femoral component 70 comprises (i) a lateral condyle (e.g., similar to condyle 30 of FIG. 3) having a substantially U-shaped configuration and having an interior surface 73 and an opposing exterior surface 75, each extending between an anterior end 77*a* and an opposing posterior end 77*b*; and (ii) a medial condyle (e.g., similar to condyle 28 of FIG. 3) having a substantially U-shaped configuration and having an interior surface 73 and an opposing exterior surface 75 each extending between an anterior end 77*a* and an opposing posterior end 77*b*, the medial condyle being connected to the lateral condyle such that an elongated slot is formed between the lateral condyle and the medial condyle.

A first engagement lip 78*a* projects from the interior surface 73 of at least the lateral condyle or the medial condyle at the anterior end 77*a* thereof; and a second engagement lip 78*b* projects from the interior surface of at least the lateral condyle or medial condyle at the posterior end 77*b* thereof.

Mating lips 78a-b and grooves are an example of a mating relationship between the femoral component 70 and the resected femur 74 that maintains the femoral component 70 on the resected femur 74. Other examples of such a mating relationship include an embodiment in which a single mating lip extends from a U-shaped main body into a single groove on a resected femur.

Thus, femoral component 70 comprises a main body 71 having an interior surface 73 and an opposing articulating surface 75 each extending between a lateral side and a medial side, the interior surface 73 having a substantially U-shaped transverse cross section; and at least one and preferably first and second lips 78a-b projecting inwardly from the anterior or posterior end of the interior surface 73 of the body 71.

Cuts are formed on resected femoral surface 72 complementary to interior surface 73 with respective complimentary mating grooves 79a-b being formed to receive respective lips 78a-b. In this configuration, femoral component 70 can be laterally slid onto femur 74 so that lips 78a-b are received within the corresponding grooves 79a-b on femur 74, thereby securing femoral component 70 to femur 74.

Another method for resurfacing a femur thus comprises: (i) resecting an articulating surface at a distal end of a femur 74 so as to form a resected articular surface 72 having an anterior surface and a posterior surface each extending between a lateral side and a medial side, at least one of the anterior surface and posterior surface having a groove 79a-b therein; and (ii) sliding a femoral component 70 onto the resected articular surface 72, a lip 78a-b of the femoral component 70 mating with the groove 79a-b, the femoral component 70 being slid medial to lateral or lateral to medial.

As shown in FIG. 7, the step of resecting an articulating surface preferably comprises forming first and second opposing grooves 79a-b in the resected articular surface 72 and wherein first and second lips 78a-b of the femoral component 70 are slid into respective grooves 79a-b, the first and second lips 78a-b being slid medial to lateral or lateral to medial.

FIG. 8 shows a tapered relationship between a femoral component 80 and a resected femur 90, which is another example of a mating relationship between a femoral component 80 and a resected femur 90 that maintains the femoral component 80 on a tapered resected surface 88 of a resected femur 90.

FIG. 8 is a perspective view of a femoral component 80 having an exterior surface 82 and a tapered interior surface 84 that is being mounted in the direction of arrow 89 onto a resected femur 90 having a complimentary, tapered, mating resected surface 88, thereby securing the femoral component 80 to the resected femur 90.

More specifically, component 80 comprises a body 85 having an interior surface 84 and an opposing articulating surface 82, each extending between a lateral side 81 and a medial side 83. The interior surface 84 has a substantially U-shaped transverse cross section that inwardly tapers. The taper may occur from the medial side to the lateral side or from the lateral side to the medial side.

In the embodiment of FIG. 8, U-shaped femoral component 80 is formed wherein the U-shaped cavity bounded by the femoral component constricts, i.e., decreases in size, medial to lateral. (In another embodiment, the femoral component decreases in size lateral to medial and the interior surface 84 is configured with a mating surface). Femur 90 is cut in a mating configuration such that the femoral component 80 wedges onto femur 90 as the femoral component 80 is slid in the direction of arrow 89 onto femur 90 lateral to medial, thereby retaining the femoral component on femur 90.

As reflected in FIG. 8, a method for resurfacing a femur 90 comprises: (i) resecting an articulating surface at a distal end of a femur 90 so as to form a resected articular surface 88 having an anterior surface 92 and a posterior surface 94 each extending between a lateral side 96 and a medial side 98, at least one of the anterior surface 92 and posterior surface 94 being sloped relative to the other such that the anterior surface 92 and posterior surface converge toward the lateral side 96 or medial side 98; and (ii) sliding a femoral component 80 onto the resected articular surface 88, the femoral component being 80 slid lateral to medial as shown or medial to lateral.

FIG. 8a is a cross sectional view of an alternative femoral component 80a, having an articulating surface 82a and a non-chamfered, curved interior surface 84a, shown as mounted onto a resected femur 86a. Anterior and posterior lips 88a-b mate with corresponding grooves 89a-b in femur 86a. FIGS. 7 and 8A demonstrate that a femoral component having inwardly projecting lips 88a-b can have a variety of different interior surfaces. The interior surface 84a of the femoral component of FIG. 8A can also be tapered similarly to FIG. 7 so as to mate with a complimentary tapered resected femur, as discussed with reference to FIG. 7.

As another feature of the present invention, FIGS. 9-14 depict connectible two-piece end use femoral components 102, 131, 161, and 191 used in knee arthroplasty wherein the two parts are readily, independently slid in from the medial or lateral side through an incision and then connected and mounted onto a femoral resection. Optionally, one part may be mounted on the femoral resection followed by another part being connected thereto. An attachment member, such as a bolt or screw can then be inserted through the femur until contacting the femoral component. A coupling member, e.g., a bolt or a screw attaches one part of the femoral component to another. The procedure is minimally invasive and does not require as large an incision as one piece components because one part of the femoral component may be placed through the incision, followed by the other part of the femoral component.

Figure 9:
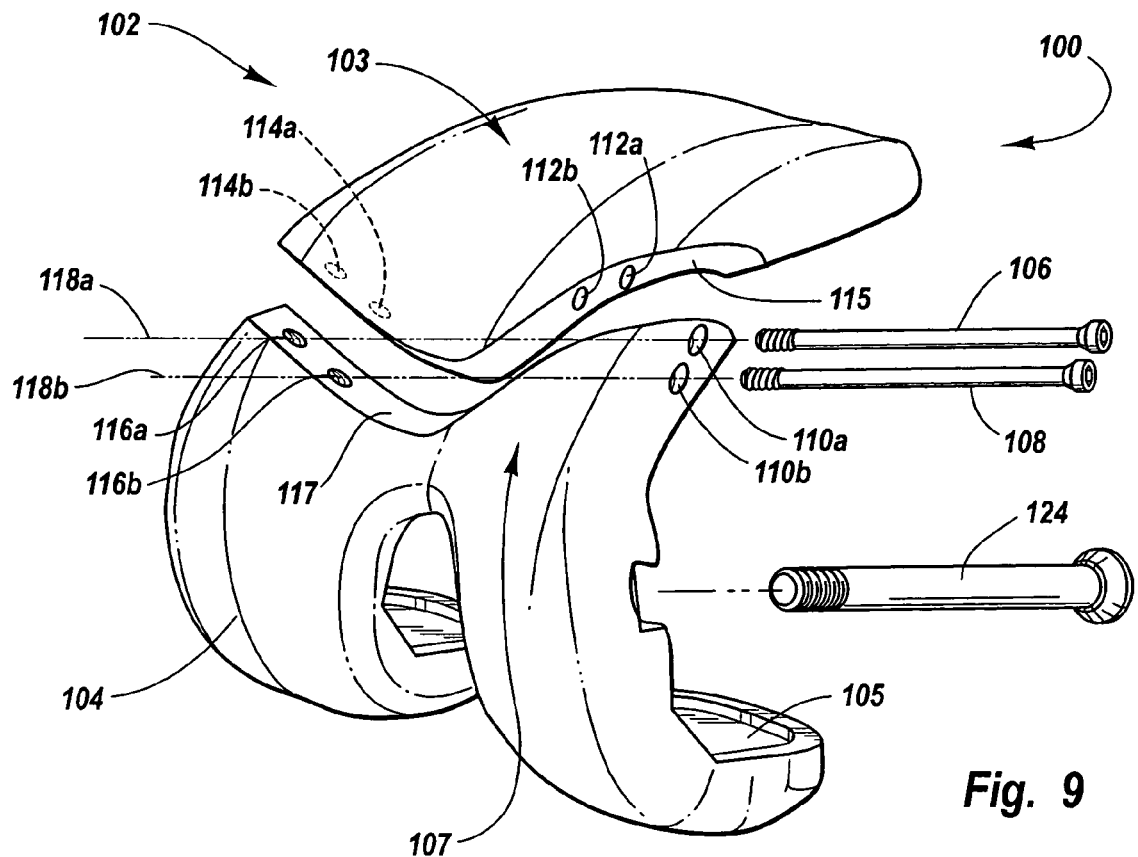
FIG. 9 is a perspective view of an alternative embodiment of a two-piece femoral component divided lateral to medial.
Figure 10:
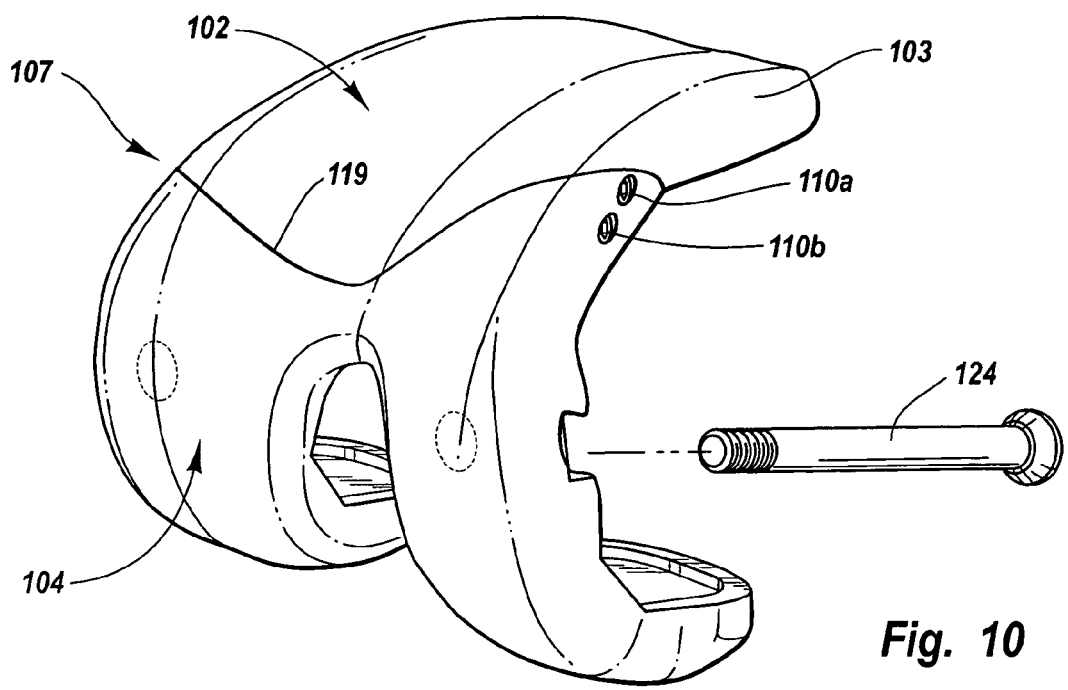
FIG. 10 is a perspective view of the femoral component shown in FIG. 9 in an assembled state.

FIG. 9 is a perspective view of a two-piece end use femoral component 102 divided lateral to medial, while FIG. 10 is a perspective view of the femoral component 102 shown in an assembled state. Femoral component 102 is configured for "end use" in that it is configured to be permanently mounted onto a resected articular surface during a resurfacing procedure so as to articulate against a tibia and/or prosthetic tibial component and is designed for actual daily use by a patient who has experienced the procedure in order to replace at least a portion of a knee.

FIG. 9 thus depicts a femoral knee prosthesis system 100 for resurfacing a resected articular surface at the distal end of a femur, comprising: end use femoral component 102 having (A) an interior surface 105 adapted to mate with the resected articular surface and (B) an opposing articulating surface 107.

The end use femoral component further comprises (i) a first portion, i.e., patellar condyle 103, comprising a first section of the articulating surface; (ii) a second portion, i.e., tibial condyle 104 comprising a second section of the articulating surface, the second portion 104 being selectively mateable with the first portion 103; and (iii) bolts 106, 108 configured to selectively connect the first portion 103 to the second portion 104. Bolts 106, 108 are examples of means for selectively connecting the first portion to the second portion. Bolt 124 secures the femoral component 102 to the femur using the same method as previously discussed with regard to FIGS. 3, 4, and 6. However, a variety of other methods may be employed to secure the femoral component to the femur, such as the use of bone cement or pegs compressed into the resected femur. In one embodiment, at least a portion of patellar condyle 103 corresponds to an anterior portion of the resected femur while at least a portion of tibial condyle 104 corresponds to a posterior portion of the resected femur.

As shown, bolts 106, 108 extend through respective apertures 110a-b, 112a-b, 114a-b, 116a-b along orientation lines 118a-b to connect portions 103, 104 such that the combined condyle portions 103, 104 collectively form the femoral component 102 shown in FIG. 10.

U-shaped femoral component 102 is divided along a joint 119 so that femoral component 102 comprises an anterior section 115 and a posterior section 117. At least one and preferably first and second passageways defined by apertures 110a-b, 112a-b, 114a-b, and 116a-b extend laterally through both anterior section 115 and posterior section 117 such that when sections 115 and 117 are aligned, threaded bolts 106, 108 can be laterally threaded into the passageways so as to secure the mating sections.

During a resurfacing procedure, the first and second portions 103, 104 are readily, independently slid in from the medial or lateral side through an incision and then connected and mounted onto a femoral resection. Optionally, one part 103 or 104 may be mounted on the femoral resection followed by the mating part being connected thereto and mounted on the femoral resection.

A method for resurfacing a femur employing femoral component 102 thus comprises (i) resecting an articulating surface at a distal end of a femur so as to form a resected articular surface; (ii) positioning a first portion 103 of an end use femoral component on or adjacent to the resected articular surface, the first portion 103 comprising a first section of an articulating surface of the end use femoral component 102; (iii) positioning a second portion 104 of the end use femoral component 102 on or adjacent to the resected articular surface, the second portion comprising a second section of the articulating surface of the end use femoral component 102; (iv) securing the first portion 103 of the end use femoral component 102 to the second portion of the end use femoral component; and (v) attaching the end use femoral component 102 to the resected articular surface, e.g., through the use of bolt 124, a screw, pin or other means for attaching.

Figure 11:
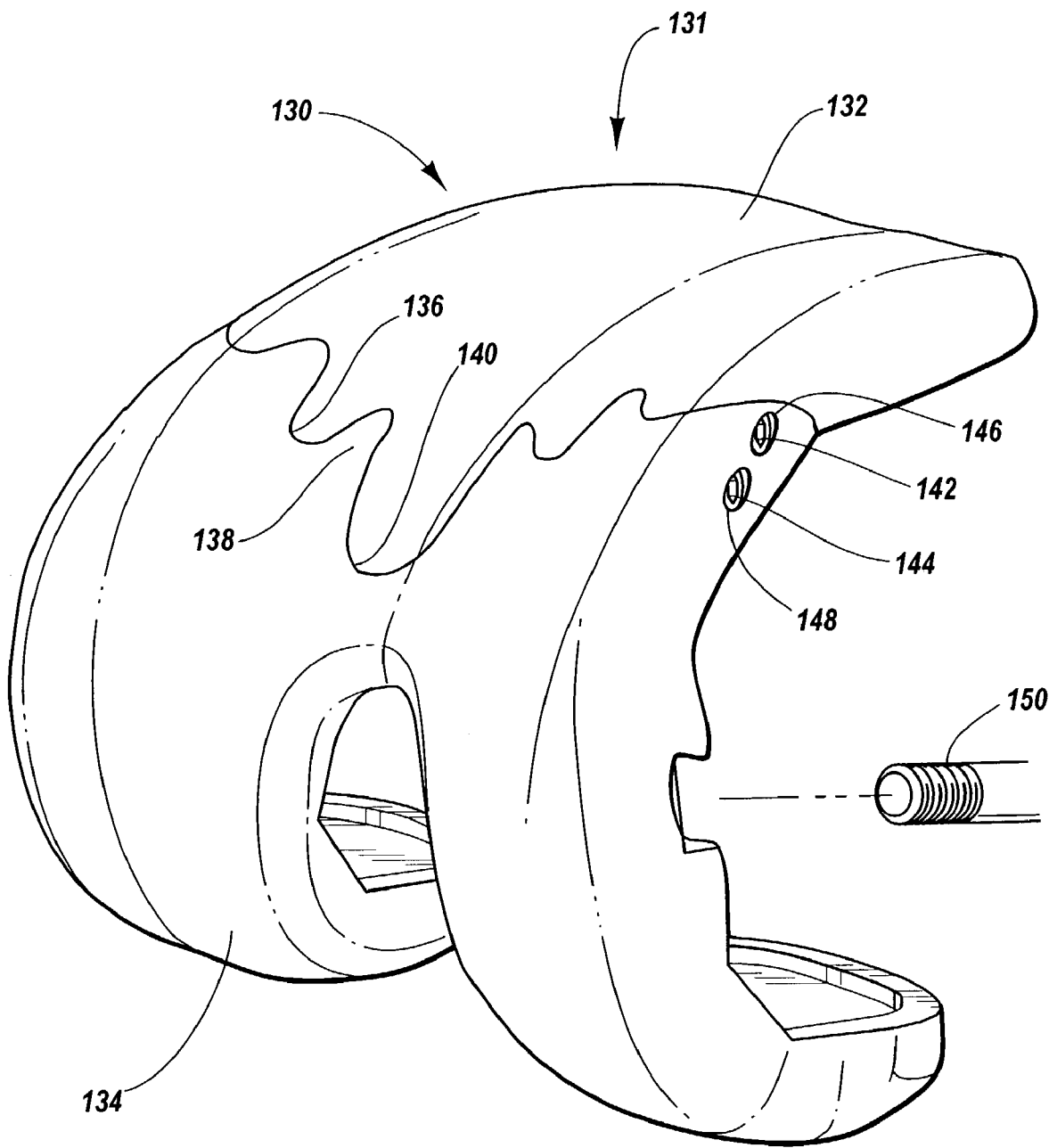
FIG. 11 is a perspective view of a two-piece femoral component having meshing teeth and divided lateral to medial.

FIG. 11 is a perspective view of a system 130 comprising a substantially similar femoral component 131 having meshing teeth 136, 138 and divided lateral to medial. Component 131 comprises (i) a first portion, i.e., patella condyle 132, comprising a first section of the articulating surface; (ii) a second portion, i.e., tibial condyle 134 comprising a second section of the articulating surface, the second portion 134 being selectively mateable with the first portion 132; and (iii) bolts 142, 144 configured to selectively connect the first portion 132 to the second portion 134 by extending through respective apertures 146, 148 and additional apertures not shown. Bolts 142, 144 are examples of means for selectively connecting the first portion to the second portion. Bolt 150 is an example of means for securing the femoral component 131 to the femur.

As opposed to the smooth joint 119 of FIG. 10, femoral component 131 can be formed with a joint 140 having complementary mating teeth 136, 138.

Figure 12:
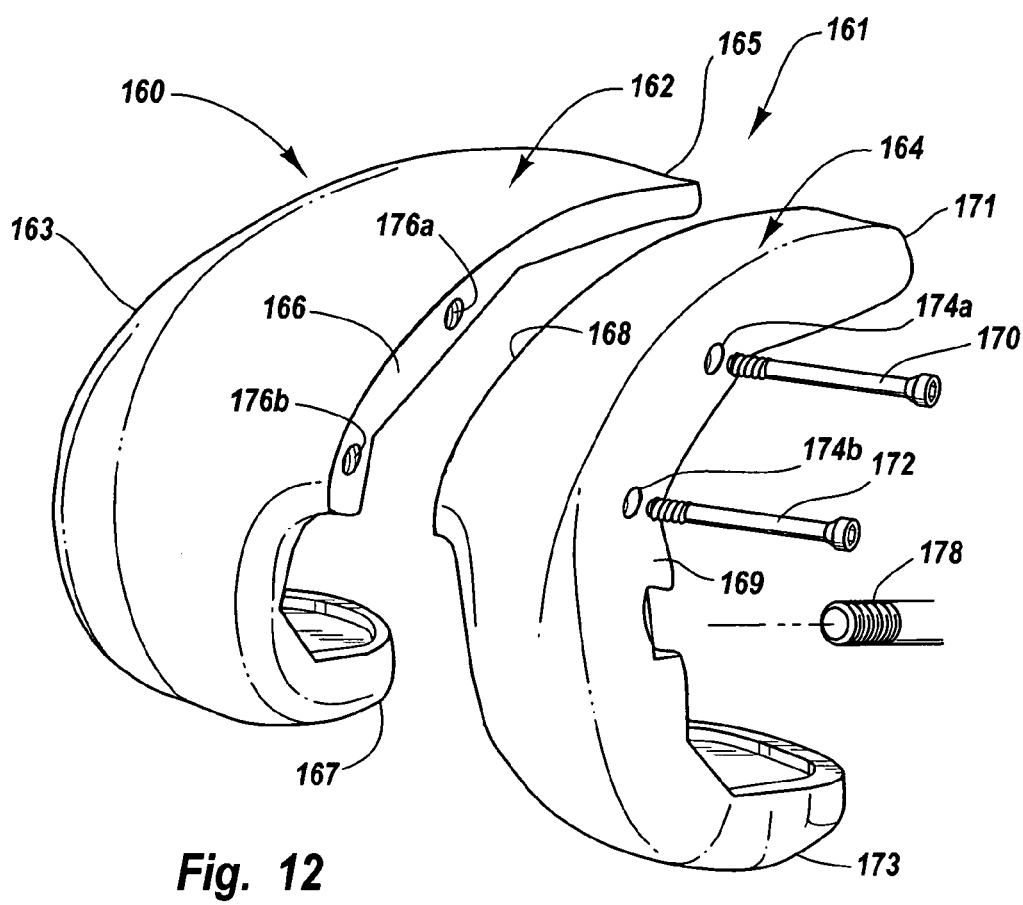
FIG. 12 is a perspective view of a two-piece femoral component divided anterior to posterior.
Figure 13:
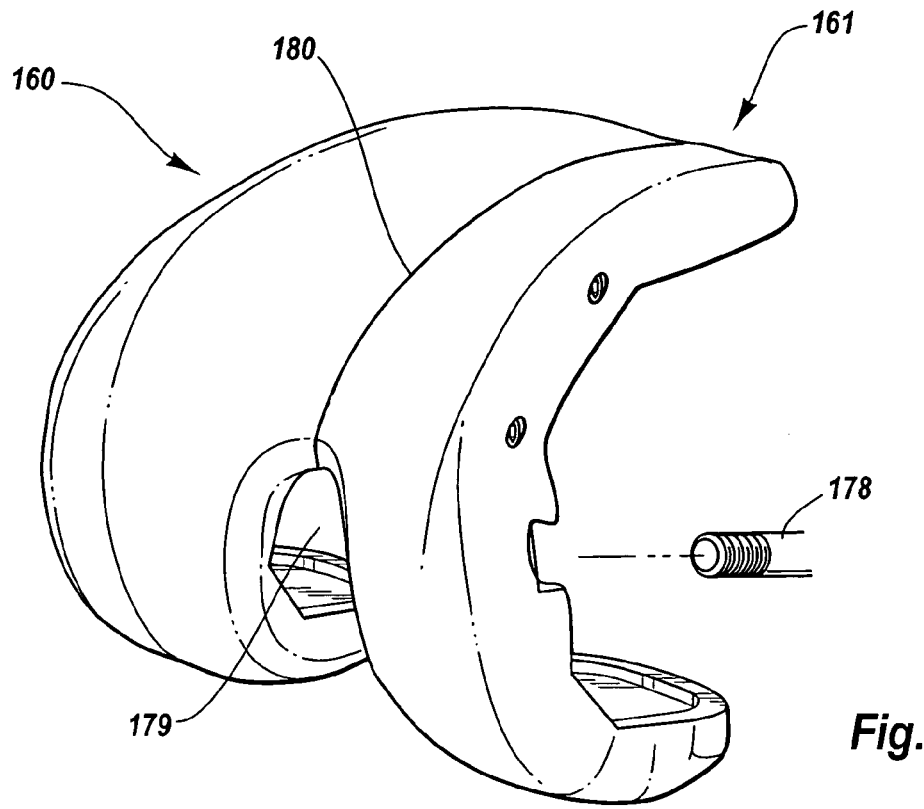
FIG. 13 is a perspective view of the femoral component shown in FIG. 12 in an assembled state.

In yet another embodiment, as discussed with respect to FIGS. 12 and 13, the first portion comprises a substantially U-shaped lateral condyle (162) and the second portion comprises a substantially U-shaped medial condyle (164).

FIG. 12 is a perspective view of a femoral component 161 of system 160 divided anterior to posterior and FIG. 13 is a perspective view of the femoral component 161 shown in FIG. 12 in an assembled state.

Femoral component 161 comprises: (i) a lateral condyle 162 having a substantially U-shaped configuration and having a lateral side 163 and an opposing medial side 166 each extending between an anterior end 165 and an opposing posterior end 167; (ii) a medial condyle 164 having a substantially U-shaped configuration and having a lateral side 168 and an opposing medial side 169 each extending between an anterior end 171 and an opposing posterior end 173. The lateral side 168 of the medial condyle 164 is configured to mate with the medial side 166 of the lateral condyle 162 such that a slot 179 is formed between the medial condyle and the lateral condyle at the posterior ends thereof.

Bolts 170, 172 are examples of means for connecting the medial condyle to the lateral condyle when the medial condyle and lateral condyle are mated. Bolt 178 secures the femoral component 161 to the femur. However, a variety of other methods may be employed to secure the femoral component to the femur, such as the use of bone cement or pegs compressed into the resected femur.

Femoral component 161 is centrally divided anterior to posterior along a linear joint 180 so that femoral component 161 comprises a medial section and a lateral section. At least one and preferably first and second passageways defined by apertures 174a-b and 176a-b extend laterally through both the medial section and the lateral section such that when the sections are aligned, bolts 170, 172 can be laterally threaded into respective passageways so as to secure the sections together.

Figure 14:
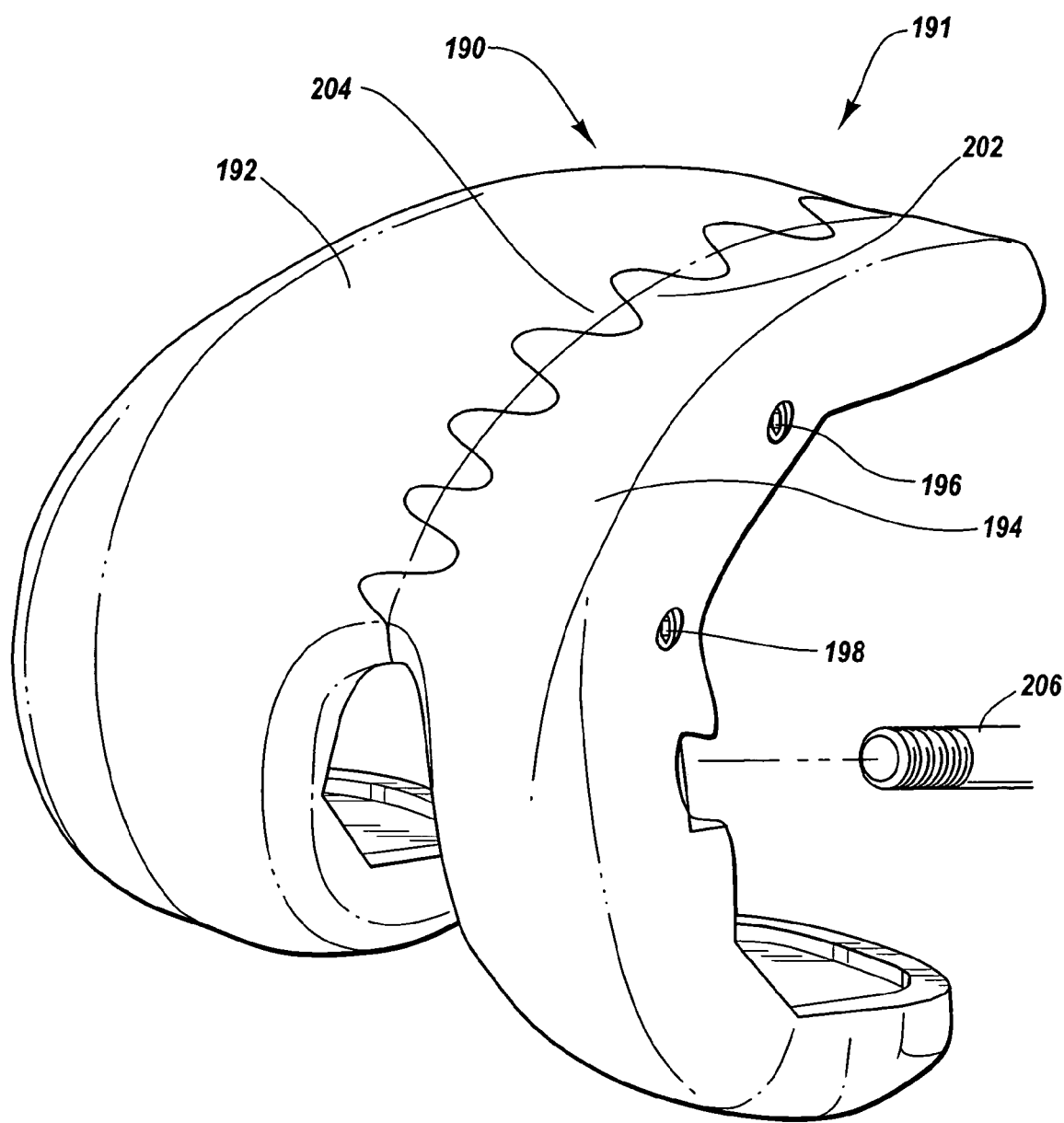
FIG. 14 is a perspective view of a femoral component divided anterior to posterior and having meshing teeth.

FIG. 14 is a perspective view of a femoral component divided anterior to posterior and having meshing teeth. FIG. 14 shows a system 190 comprising a substantially similar femoral component 191 having meshing teeth 202, 204 and divided anterior to posterior. Component 191 comprises (i) a first portion, i.e., lateral condyle 192, comprising a first section of the articulating surface; (ii) a second portion, i.e., medial condyle 194 comprising a second section of the articulating surface, the second portion being selectively mateable with the first portion; and (iii) bolts 196, 198 configured to selectively connect the first portion to the second portion. Bolts 196, 198 are examples of means for selectively connecting the first portion to the second portion. Bolt 206 or other method of attachment can be employed to secure the femoral component 191 to the femur.

As depicted in FIG. 14, in contrast to having a linear joint, femoral component 191 can be formed with a joint having complementary mating teeth formed on each of the sections.

FIGS. 15A-16B demonstrate assembled and exploded views of another two-piece femoral component of the present invention employing protrusions in order to link the pieces of the component. The two parts are readily, independently slid in from the medial or lateral side through an incision and then connected and mounted onto a femoral resection. Optionally, one part may be mounted on the femoral resection followed by another part being connected thereto and mounted on the femoral resection.

FIG. 15 depicts a femoral knee prosthesis system 210 for resurfacing a resected articular surface at the distal end of a femur, comprising: (i) end use femoral component 211 having (i) an interior surface 215 adapted to mate with the resected articular surface and (ii) an opposing articulating surface 217.

The end use femoral component 211 comprises (i) a first portion, i.e., patellar condyle 214, comprising a first section of the articulating surface; and (ii) a second portion, i.e., tibial condyle 212 comprising a second section of the articulating surface, the second portion 212 being selectively mateable with the first portion 214. Specifically, second portion 212 of femoral component 211 has an interior surface 261, an opposing articulating surface 263, and a peripheral edge 264 extending between surfaces 261 and 263. Peripheral edge 264 includes an outside edge 266 and a recessed substantially U-shaped mating surface 266. Protrusions 224-230 project from mating surface 266 of second portion 212 and are configured to be received within first portion 214, thereby mating the first and second portions. In the embodiment depicted protrusions 224-230 have a substantially cylindrical configuration. Passages 242 and 242a extend from outside edge 266 to mating surface 266 an opposing sides of second portion 212. Pegs 220-222 project from interior surface 261 and are additional examples of means for securing the femoral component 211 to the femur.

First portion 214 of femoral component 211 also has an interior surface 268, an opposing articulating surface 270, and a peripheral edge 272 extending between surfaces 268 and 270. Peripheral edge 272 includes an outside edge 273 and a mating surface 274. Mating surface 274 has an outwardly projecting, substantially U-shaped configuration that is substantially complementary to mating surface 266 of second portion 212. Four spaced apart apertures 232, 238, 239 (fourth aperture not shown) are formed on mating surface 274 and are configured to receive corresponding protrusions 224-230. In the embodiment depicted, each aperture comprises a substantially cylindrical blind socket bounded by an encircling sidewall. Threaded apertures 244 and 244a are formed on opposing sides of mating surface 274 so that threaded apertures 244 and 244a are aligned with passages 242 and 242a when first portion 214 is coupled with second portion 212.

Femoral knee prosthesis system 210 further comprises bolts 240, 240a or screws that are configured to connect first portion 214 to second portion 212 once the protrusions 224-230 are mounted in first portion 214. In one embodiment, an incision is made in only one side of the knee. Thus, only one of bolts 240 or 240a is employed to connect first portion 214 to second portion 212.

Figure 15A:
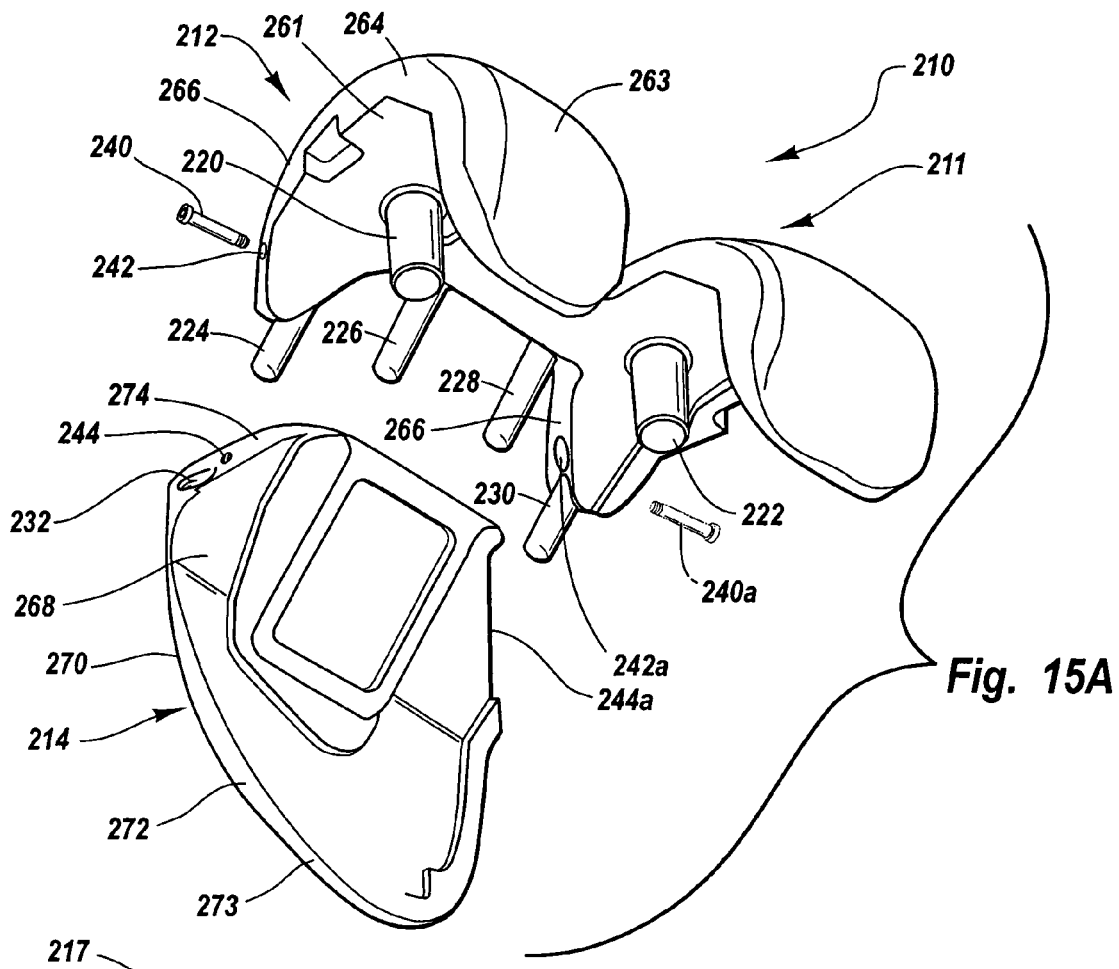
FIGS. 15A-16B demonstrate assembled and exploded views of another two-piece femoral component of the present invention.
Figure 15B:
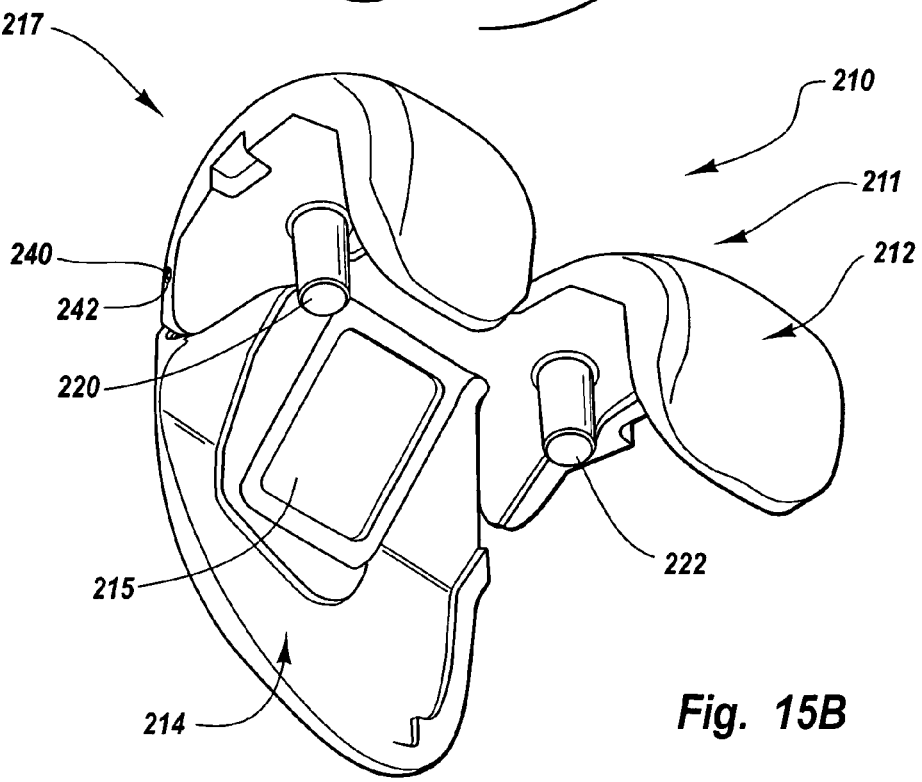
Figure 16A:
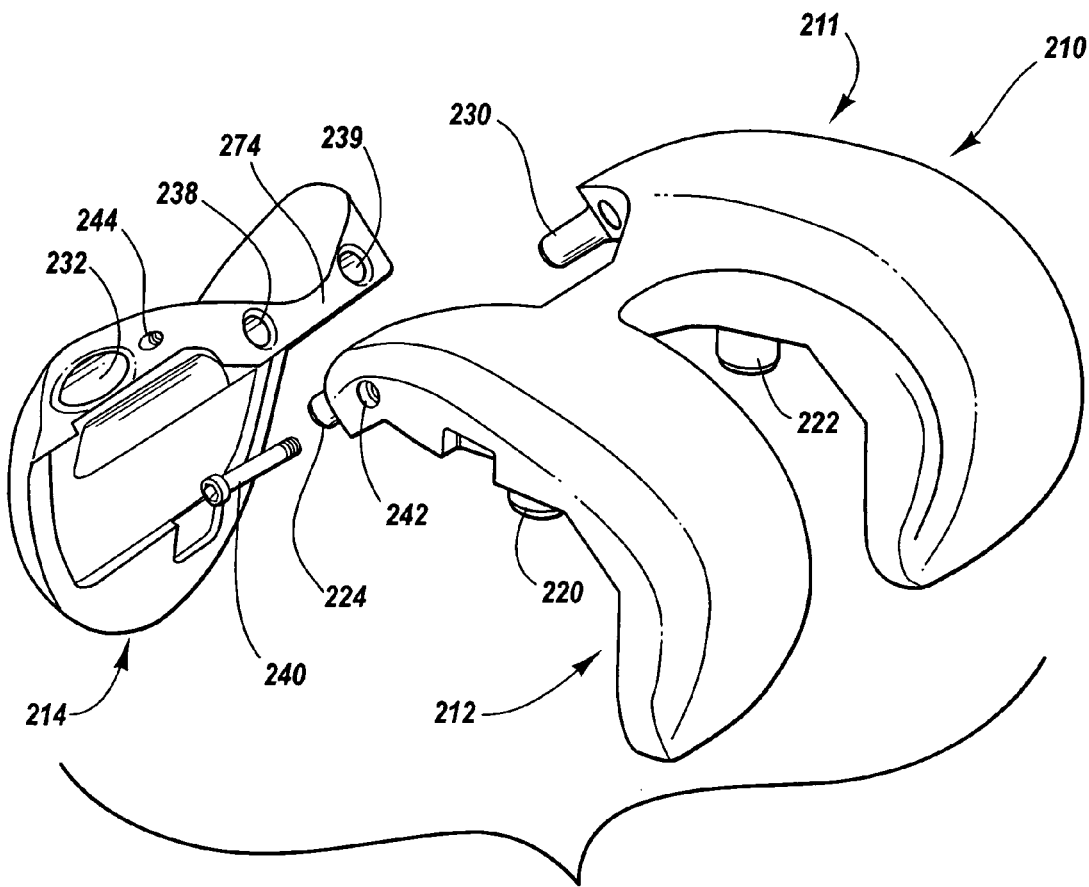
Figure 16B:
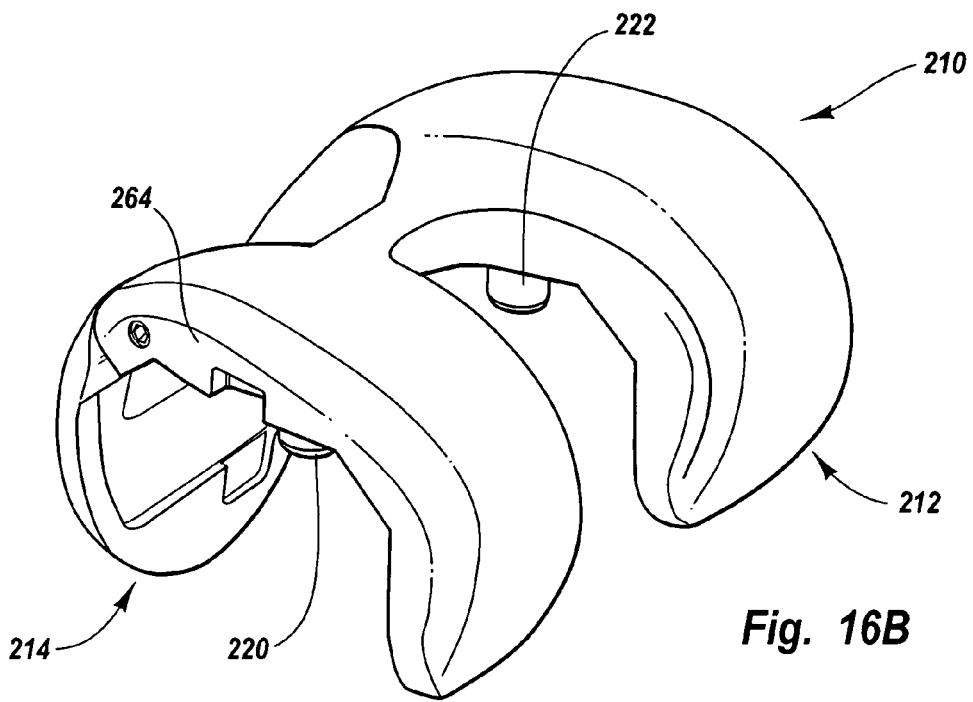

As shown, protrusions 224-230 extend through respective apertures 232, 238, 239 (fourth aperture not shown) and bolt 240 is extended through passage 242 and into bored aperture 244 such that the combined condyle portions 214, 212 collectively form the femoral component 211 shown in FIGS. 15B and 16B. The use of protrusions 224-230 and at least one bolt 240 forms a strong connection between first and second portions 214, 212. Bolt 240a is extended through aperture 242a and into bored aperture 244a in portion 214.

As discussed above, the femoral components of the present invention are conveniently slid in from the medial or lateral side through an incision. In addition, the femoral components of the present invention may be conveniently slid (either as one piece or two-piece members) through and incision in between the medial and lateral sides. The femoral components are designed to articulate against the tibia and/or a prosthetic tibial component.

It is appreciated that the various configurations, structures, and methods as discussed above can be mixed and matched to form yet other unique configurations, structures, and methods.

Additional disclosure relating to apparatuses and methods of the present invention is available in a U.S. patent application Ser. No. 10/445,288, filed May 23, 2003 entitled "Modular Femoral Components for Knee Arthroplasty" with Daniel F. Justin and E. Marlowe Goble as inventors, which application is incorporated herein in its entirety by reference.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A femoral knee prosthesis system for resurfacing a resected articular surface at the distal end of a femur, the prosthesis system comprising:

a first femoral component portion having a first interior surface adapted to mate with the resected articular surface of the femur, an opposing first articulating surface, and a first mating surface that extends between the first interior surface and the first articulating surface;

a second femoral component portion having a second interior surface adapted to mate with the resected articular surface of the femur, an opposing second articulating surface, and a second mating surface that extends between the second interior surface and the second articulating surface, the second femoral component portion comprising a substantially U-shaped lateral condyle and a substantially U-shaped medial condyle with a channel formed therebetween, the second femoral component being an integral, unitary member;

a first blind socket and a spaced apart second blind socket formed on the first mating surface or the second mating surface, the first blind socket and the second blind socket each being bounded by an encircling sidewall;

a first projection and a spaced apart second projection projecting from the first mating surface or the second mating surface such that the first projection and the second projection can be selectively received within the first blind socket and the second blind socket so as to mate the first femoral component portion with the second femoral component portion; and means for securely connecting the first femoral component portion to the second femoral component portion when the first projection and the second projection are received within the first blind socket and the second blind socket;

the first femoral component portion and the second femoral component portion forming an end use femoral component when connected together.

2. The femoral knee prosthesis system recited in claim 1, wherein the first projection and the second projection each have a substantially cylindrical configuration.

3. The femoral knee prosthesis system recited in claim 1, further comprising:

a third blind socket formed on the first mating surface or the second mating surface;

a third projection projecting from the first mating surface or the second mating surface such that the third projection is received within the third blind socket when the first femoral component portion is mated with the second femoral component portion.

4. The femoral knee prosthesis system recited in claim 1, wherein the means for securely connecting the first femoral component portion to the second femoral component portion comprises a first fastener that extends through a section of the second femoral component portion and into a section of the first femoral component portion.

5. The femoral knee prosthesis system recited in claim 4, wherein the first fastener is spaced apart from the first projection and the second projection.

6. The femoral knee prosthesis system recited in claim 4, further comprising:

the second femoral component portion having an outside edge that extends between the second interior surface and the second articulating surface, a passage extending through the second femoral component portion from the outside edge to the second mating surface; and an aperture formed on the first mating surface of the first femoral component portion, the first fastener extending through the passage and into the aperture.

7. The femoral knee prosthesis system recited in claim 4, wherein the first fastener has threads that threadedly engage with the first femoral component portion.

8. The femoral knee prosthesis system recited in claim 4, further comprising a second fastener that extends through a section of the second femoral component portion and into a section of the first femoral component portion, the second fastener being disposed on a side of the first femoral component portion opposite the first fastener.

9. The femoral knee prosthesis system recited in claim 1, wherein the first mating surface has an outwardly projecting substantially U-shaped configuration and the second mating surface has a recessed substantially U-shaped configuration that is substantially complementary to the first mating surface.

10. The femoral knee prosthesis system recited in claim 1, wherein the first femoral component portion and second femoral component portion combine to form a femoral component, the system further comprising means for securing the femoral component to the femur.

11. The femoral knee prosthesis system recited in claim 10, wherein the means for securing the femoral component to the femur comprises a post projecting from the first interior surface of the first femoral component portion or from the second interior surface of the second femoral component portion.

12. A femoral knee prosthesis system for resurfacing a resected articular surface at the distal end of a femur, the prosthesis system comprising:

a first femoral component portion having a first interior surface adapted to mate with the resected articular surface of the femur, an opposing first articulating surface, and a first mating surface that extends between the first interior surface and the first articulating surface;

a second femoral component portion having a second interior surface adapted to mate with the resected articular surface of the femur, an opposing second articulating surface, and a second mating surface that extends between the second interior surface and the second articulating surface, the second femoral component portion comprising a substantially U-shaped lateral condyle and a substantially U-shaped medial condyle with a channel formed therebetween, wherein one of the first mating surface or the second mating surface has an outwardly projecting substantially U-shaped configuration and the other of the first mating surface or the second mating surface has a complementary recessed substantially U-shaped configuration, the second femoral component being an integral, unitary member;

a first blind socket and a spaced apart second blind socket formed on the first mating surface or the second mating surface, the first blind socket and the second blind socket each being bounded by an encircling sidewall;

a first projection and a spaced apart second projection projecting from the first mating surface or the second mating surface such that the first projection and the second projection can be selectively received within the first blind socket and the second blind socket so as to mate the first femoral component portion with the second femoral component portion; and a threaded first fastener securing the first femoral component portion to the second femoral component portion when the first projection and the second projection are received within the first blind socket and the second blind socket, the first fastener being spaced apart from the first projection and the second projection;

the first femoral component portion and the second femoral component portion forming an end use femoral component when secured together.

13. The femoral knee prosthesis system recited in claim 12, wherein the first projection and the second projection each have a substantially cylindrical configuration.

14. The femoral knee prosthesis system recited in claim 12, further comprising:

a third blind socket formed on the first mating surface or the second mating surface;

a third projection projecting from the first mating surface or the second mating surface such that the third projection is received within the third blind socket when the first femoral component portion is mated with the second femoral component portion.

15. The femoral knee prosthesis system recited in claim 12, further comprising:

the second femoral component portion having an outside edge that extends between the second interior surface and the second articulating surface, a passage extending through the second femoral component portion from the outside edge to the second mating surface; and an aperture formed on the first mating surface of the first femoral component portion, the first fastener extending through the passage and into the aperture.

16. The femoral knee prosthesis system recited in claim 12, further comprising a threaded second fastener securing the first femoral component portion to the second femoral component portion, the second fastener being disposed on a side of the first femoral component portion opposite the first fastener.

17. The femoral knee prosthesis system recited in claim 12, wherein the first femoral component portion and second femoral component portion combine to form a femoral component, the system further comprising means for securing the femoral component to the femur.

18. The femoral knee prosthesis system recited in claim 17, wherein the means for securing the femoral component to the femur comprises a post projecting from the first interior surface of the first femoral component portion or from the second interior surface of the second femoral component portion.

* * * * *

UNITED STATES PATENT AND TRADEMARK OFFICE
CERTIFICATE OF CORRECTION

| | | |
|---|---|---|
| PATENT NO. | : 7,615,081 B2 | Page 1 of 1 |
| APPLICATION NO. | : 10/444927 | |
| DATED | : November 10, 2009 | |
| INVENTOR(S) | : Justin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 196 days.

Signed and Sealed this

Nineteenth Day of October, 2010

David J. Kappos
*Director of the United States Patent and Trademark Office*